(12) United States Patent
Moakler et al.

(10) Patent No.: US 9,804,051 B2
(45) Date of Patent: Oct. 31, 2017

(54) EROSION DETECTION OF ROTATING EQUIPMENT WITH HARMONIC FREQUENCIES

(71) Applicant: SCHLUMBERGER TECHNOLOGY CORPORATION, Sugar Land, TX (US)

(72) Inventors: Dean Moakler, Bixby, OK (US); Rajesh Luharuka, Katy, TX (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 135 days.

(21) Appl. No.: 14/605,279

(22) Filed: Jan. 26, 2015

(65) Prior Publication Data
US 2016/0216171 A1 Jul. 28, 2016

(51) Int. Cl.
G01M 1/22 (2006.01)
G01N 29/02 (2006.01)
E21B 21/06 (2006.01)

(52) U.S. Cl.
CPC .............. *G01M 1/22* (2013.01); *E21B 21/062* (2013.01); *G01N 29/02* (2013.01)

(58) Field of Classification Search
CPC ........ G01M 1/22; G01N 29/02; E21B 21/062; E21B 43/00; B01F 3/12; B01F 15/00
See application file for complete search history.

(56) References Cited

U.S. PATENT DOCUMENTS

| | | | |
|---|---|---|---|
| 5,215,763 A * | 6/1993 | Mattera | B29B 9/065 264/142 |
| 6,491,422 B1 | 12/2002 | Rutten et al. | |
| 2004/0194539 A1 | 10/2004 | Gysling | |
| 2006/0152998 A1 * | 7/2006 | Burr | B01F 11/0005 366/116 |
| 2008/0141780 A1 | 6/2008 | Wavering et al. | |
| 2008/0210212 A1 * | 9/2008 | Baratta | B23D 61/026 125/15 |
| 2010/0254212 A1 | 10/2010 | Howe et al. | |
| 2014/0069650 A1 | 3/2014 | Stegemoeller et al. | |
| 2015/0027702 A1 * | 1/2015 | Godoy-Vargas | C09K 8/90 166/279 |
| 2015/0060072 A1 * | 3/2015 | Busby | C09K 8/90 166/294 |

OTHER PUBLICATIONS

International Search Report and Written Opinion issued in International Patent Application No. PCT/US2016/013819 dated May 24, 2016; 10 pages.

* cited by examiner

*Primary Examiner* — Helen Kwok
(74) *Attorney, Agent, or Firm* — Michael L. Flynn; Rachel E. Greene; Robin Nava

(57) ABSTRACT

Method for analyzing blending mixer performance is provided, which includes providing an apparatus for blending solid particles with a liquid composition, a rotating slinger, and at least one accelerometer positioned adjacent a rotating component for producing a signal that is proportional to an acceleration of the rotating slinger over a frequency range. A recorder for receiving and storing over a time interval the signal is in communication with the accelerometer. The recorded signals are converted to numeric values indicative of a vibrational amplitude of the rotating slinger over the frequency range, and harmonics from the numerical values are identified and used to determine the condition of the rotating slinger.

21 Claims, 5 Drawing Sheets

EROSION DETECTION OF ROTATING EQUIPMENT WITH HARMONIC FREQUENCIES

FIELD

The field to which the disclosure generally relates to is monitoring apparatus for continuously mixing solid particles with liquids, and more specifically monitoring the condition of apparatus useful for mixing sand or particles similar to sand with a liquid to provide slurries for treating wellbores and surrounding subterranean formations, in petroleum recovery operations.

BACKGROUND

The statements in this section merely provide background information related to the present disclosure and may not constitute prior art.

Apparatus are employed as continuously blending mixers, in which sand, sand-like particles, or other particulate solids are mixed (or blended) with a gel or slickwater composition, and the resulting slurry is pressurized by the mixer itself. A typical use for the resulting slurry is as a treating fluid, which is introduced into a well to enhance recovery of a petroleum product. The blending mixers typically have has a slinger element of a toroidal configuration with a concave upper surface. Several upstanding blade members are mounted on the concave surface of this slinger and an impeller member is attached to the underside of the slinger. The slinger and the impeller are enclosed within a housing and fastened to the end of a drive shaft rotated by a motor mounted above the housing. A hopper is mounted above an inlet eye in the top of the housing, for introducing sand or the other sand-like particles into the housing. At the bottom of the housing is a suction eye inlet, for drawing liquid into the housing, and the resulting liquid-solid mixture is discharged through an outlet port in the housing.

In a continuous blending operation the objective is to be able to prepare a slurry of particulate material (such as sand or other propping agents) and liquid (the gel composition, or other liquid, such as water) and pressurizing the resulting slurry to a desired level. In the operation of the blending mixer, sand flows out of the hopper in a continuous stream and drops onto the rotating slinger through the inlet eye in the housing. With the impeller and slinger rotating at the same speed, the vortex action of the impeller creates a suction force that draws the gel composition into the casing through the suction eye inlet. As the gel is pulled into the mixing casing it is pressurized by the impeller and it mixes thoroughly with the sand being flung outwardly, in a centrifugal action, from the slinger. The sand-gel mixture is then continuously discharged, under pressure, through the outlet port, from which it is carried into a pumper unit and injected into a well.

The structure of the mixing impeller can create a significant resistance in the flow of solids, and the large surface area of the impeller which also has a very close fit within the mixing casing contributes to frictional drag and erosion of the impeller and other parts of the blending mixer. Further, the liquid composition can become trapped inside the rotating impeller, and as the solids to liquid ratio increases, the performance of the blending mixer may decline rapidly in operation. When sufficient loss of performance or erosion of the impeller occurs, in some cases, injection of the slurry into the well may decrease or cease, leading to interruption of a treatment operation in a subterranean formation penetrated by the wellbore. The same applies to the rotating slinger, as the performance of the blending mixer may decline rapidly in operation when the slinger becomes eroded.

There is a need for improved erosion and performance monitoring of continuously blending mixers which improves or overcomes difficulties due to damage to, and erosion of, rotating components, and such need is addressed, at least in part, by embodiments described in the following disclosure.

SUMMARY

This section provides a general summary of the disclosure, and is not a necessarily a comprehensive disclosure of its full scope or all of its features.

In a first aspect of the disclosure, method of analyzing blending mixer performance is provided, where the method includes providing an apparatus for blending solid particles with a liquid composition. The apparatus includes a rotating slinger, and at least one accelerometer positioned adjacent a rotating component connected with the slinger, for producing a signal that is proportional to an acceleration of the rotating slinger over a frequency range. A recorder for receiving and storing over a time interval the signal is in communication with the accelerometer. The recorded signals are converted to numeric values indicative of vibrational amplitude of the rotating slinger over the frequency range, and harmonics from the numerical values are identified and interpreted to determine the condition of the rotating slinger. In some cases, the acceleration correlates with a centrifugal force generated by an imbalance of the rotating slinger. Also, the numeric values may be compared with baseline data set to determine the condition of the rotating slinger. In some aspects, the numeric values are compared with a p-f curve to predict a potential mode of failure.

The accelerometers may be uni-axial, biaxial or triaxial accelerometers. Where a triaxial accelerometer is utilized, a signal is also produced that is proportional to an axial acceleration in an axial direction of the rotating component over the frequency range. Such signals may also be converted to numeric values indicative of an axial vibration of the rotating component.

In another aspect of the disclosure, a method of predicting mixer failure includes providing a mixing apparatus having a rotating component, at least one accelerometer adjacent the rotating component for producing a signal that is proportional to an acceleration of the rotating component over a frequency range, and a recorder for receiving and storing the signal. The recorder is in communication with the accelerometer. The recorded signals are converted to numeric values indicative of vibrational amplitude of the rotating component over the frequency range, and harmonics from the numerical values are identified to determine the condition of the rotating component.

Yet another aspect is a method of analyzing blending mixer performance which includes providing an apparatus for blending solid particles with a liquid composition. The apparatus has a rotating slinger, an electric motor for driving the rotating slinger, a variable frequency drive controlling the electric motor, and a hall effect sensor disposed between the variable frequency drive and the electric motor. The hall effect sensor produces a signal that is proportional to an acceleration of the rotating slinger, and the signal is recorded over a time interval on a recorder connected with the hall effect sensor. The recorded signals are converted to numeric values indicative of vibrational amplitude of the rotating slinger, and patterns are identified in the numerical values to determine the condition of the rotating slinger.

BRIEF DESCRIPTION OF THE DRAWINGS

Certain embodiments of the disclosure will hereafter be described with reference to the accompanying drawings, wherein like reference numerals denote like elements. It should be understood, however, that the accompanying figures illustrate the various implementations described herein and are not meant to limit the scope of various technologies described herein, and.

DETAILED DESCRIPTION

Figure 1:
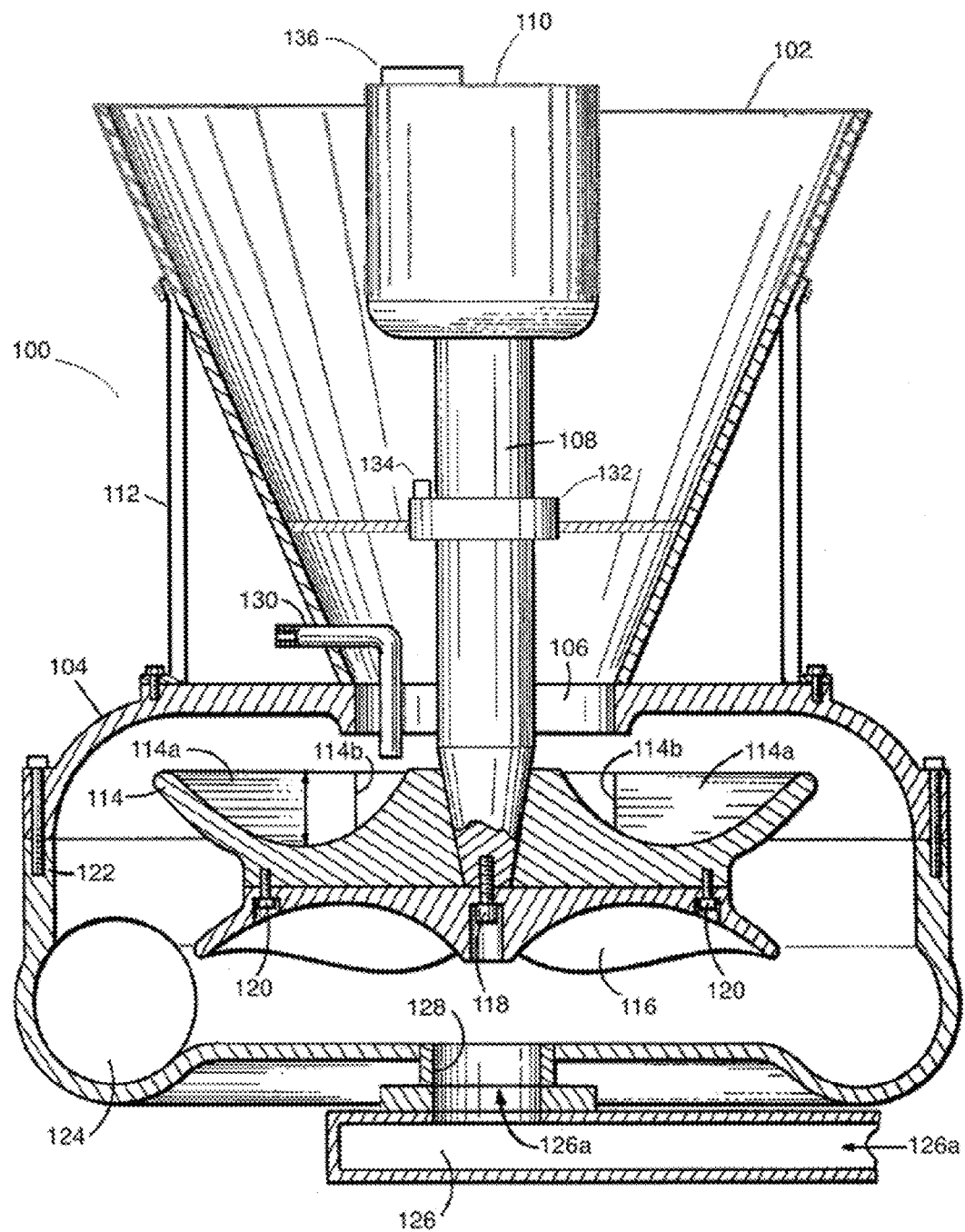
FIG. 1 illustrates general features of a blending mixer apparatus useful in some method embodiments of the disclosure, in a cross section view.

The following description of the variations is merely illustrative in nature and is in no way intended to limit the scope of the invention, its application, or uses. The description and examples are presented herein solely for the purpose of illustrating the various embodiments of the invention and should not be construed as a limitation to the scope and applicability of the invention. While the compositions of the present invention are described herein as comprising certain materials, it should be understood that the composition could optionally comprise two or more chemically different materials. In addition, the composition can also comprise some components other than the ones already cited. In the summary of the invention and this detailed description, each numerical value should be read once as modified by the term "about" (unless already expressly so modified), and then read again as not so modified unless otherwise indicated in context. Also, in the summary of the invention and this detailed description, it should be understood that a concentration or amount range listed or described as being useful, suitable, or the like, is intended that any and every concentration or amount within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific, it is to be understood that inventors appreciate and understand that any and all data points within the range are to be considered to have been specified, and that inventors possession of the entire range and all points within the range.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of concepts according to the disclosure. This description should be read to include one or at least one and the singular also includes the plural unless otherwise stated.

The terminology and phraseology used herein is for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited.

Also, as used herein any references to "one embodiment" or "an embodiment" means that a particular element, feature, structure, or characteristic described in connection with the embodiment is included in at least one embodiment. The appearances of the phrase "in one embodiment" in various places in the specification are not necessarily referring to the same embodiment.

Some embodiments according to the disclosure are useful for analyzing blending mixer performance or even predicting mixer failure. Some of such embodiments may include providing a blending or mixing apparatus having a rotating slinger for distributing solid particles into a liquid medium to form a pressurized slurry. One or more accelerometers may be disposed upon, adjacent, or otherwise in vibrational communication with a rotating component in the apparatus. The accelerometer(s) detect acceleration which correlates with a centrifugal force generated due to an imbalance in the rotating slinger. The apparatus may also include a recorder for recording the signal over a time interval while in operation. In some aspects, the methods are useful for predicting mixer failure, for a mixer having a rotating component and at least one accelerometer disposed upon or otherwise connected with the rotating component.

FIG. 1 illustrates general features of a blending mixer apparatus useful in some method embodiments of the disclosure, in a cross section view. The blending mixer apparatus is generally illustrated by the number 100. At the top of the blending mixer is a hopper 102. Hopper 102 provides a container for solid particles, such as sand, cement particulates, or other suitable proppant material and solid particles (not shown). In this embodiment the hopper 102 is mounted on the top side of the blending mixer casing 104. The hopper is disposed over an opening 106, which provides an inlet for dropping, or otherwise transferring, the sand or other solid particles into the blending mixer.

A rotating drive shaft 108 is positioned inside the hopper 102, such that the bottom of the shaft extends through the inlet eye 106 and into the casing 104. A gear box 110 for driving the shaft is mounted at the top end of the shaft 108. Gear box 110 may be driven by an suitable device, including, but not limited to, a transmission powered by an engine. The hopper 102 is connected to the top portion of the casing 104 by support braces 112. The mixer elements of the blending mixer apparatus may include a rotatable slinger member 114 and an impeller member 116. The impeller member 116 may be secured to the bottom end of the drive shaft 108 by a bolt fastener 118, or any other suitable securing device or technique.

The slinger member 114 may have a flat face which matches a corresponding flat face on the impeller member 116, and the two members, 114 and 116, are fastened together at their common faces by bolt fasteners 120 for example, or any other suitable securing device or technique. In addition, slinger member 114 has a central opening therein (not shown) which allows it to fit over the tapered end of the drive shaft 108 above the bolt fastener 118. Rotatable slinger 114 has a toroidal configuration, including a concave surface which faces toward the top of the casing 104. The impeller 116 is of a vortex configuration, with a concave surface facing toward the bottom of the casing 104. In actual practice, these design features greatly enhance thorough mixing of the solids with a liquid component. In the specific embodiment illustrated herein, the surface of slinger 114 is interrupted by several upstanding blade members 114a. As indicated in FIG. 1, the inside edge 114b of each blade is a vertical edge which is aligned approximately with the periphery of the inlet eye 106. Erosion of the features of the slinger 114 and impeller 116 may result in loss in performance of the blending mixer, and such erosion may ultimately lead to an unbalanced condition, which may manifest as vibration. Uncorrected ongoing vibration could eventually lead to operational failure of the blending mixer apparatus.

The bottom part of the blending mixer apparatus is defined by a casing bottom portion 122, which encloses the slinger 114 and impeller 116. Casing bottom portion 122 includes an outlet port 124, for the discharge of material from the casing. One end of an inlet conduit 126 is connected into the casing bottom portion 122 and the opposite end of the conduit is connected into a source for a liquid composition, such as a gel, slickwater, or other liquid. During the mixing operation the liquid composition is drawn into the casing bottom portion 122 through the inlet conduit 126, in the direction indicated by arrows 126a, and through a suction-eye inlet 128 at the bottom of the casing bottom portion 122. Means for venting gases from the blending mixer apparatus may be provided by a breather tube 130, which is installed in the top casing 104. As shown in FIG. 1, the interior end of breather tube 130 may be positioned within the periphery of the inlet eye 106, with the exterior end being positioned such that it communicates with the atmosphere exterior to casing 104.

Drive shaft 108 is secured within and passes through bearing 132. Disposed upon bearing 132, adjacent drive shaft 108, is accelerometer 134. While one accelerometer is shown, it is within the scope and spirit of the disclosure that any suitable number of accelerometers may be used. While accelerometer 134 is shown disposed upon bearing 132, adjacent drive shaft 108, the accelerometer(s) may be positioned at any functional point within blending mixer apparatus 100. In some aspects, accelerometer 134 produces a signal that is proportional to an acceleration of the rotating slinger 114 over a frequency range. Signals produced by accelerometer 134 are transmitted to recorder 136 which receives the signals over a time interval. One type of accelerometer useful for the vibration detection is a piezoelectric accelerometer. A piezoelectric accelerometer has wide frequency and dynamic ranges with good linearity throughout the ranges. It is relatively robust and reliable so that its characteristics remain stable over a long period of time. Additionally, the piezoelectric accelerometer is self-generating, not requiring a power supply, and its acceleration proportional output can be integrated to give velocity and displacement proportional signals. Generally, the accelerometers may be uni-axial, bi-axial, or tri-axial. For example, tri-axial accelerometers measure the vibration in three axes X, Y and Z, and often have three crystals positioned so that each one reacts to vibration in a different axis, thus providing three signals, each representing the vibration for one of the three axes. For uni-axial and bi-axial, one and two signals are generated, respectively.

Figure 2A:
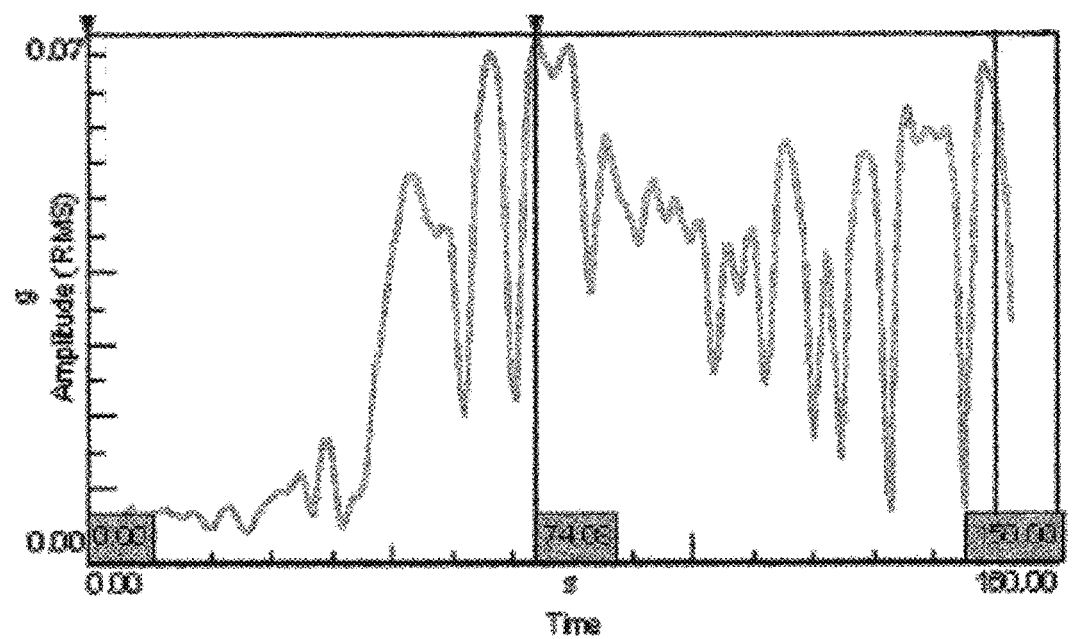
FIGS. 2A and 2B depict how vibrational amplitude may be plotted over time at a given frequency, and vibrational amplitude may be plotted over the frequency range, in accordance with the disclosure.
Figure 2B:
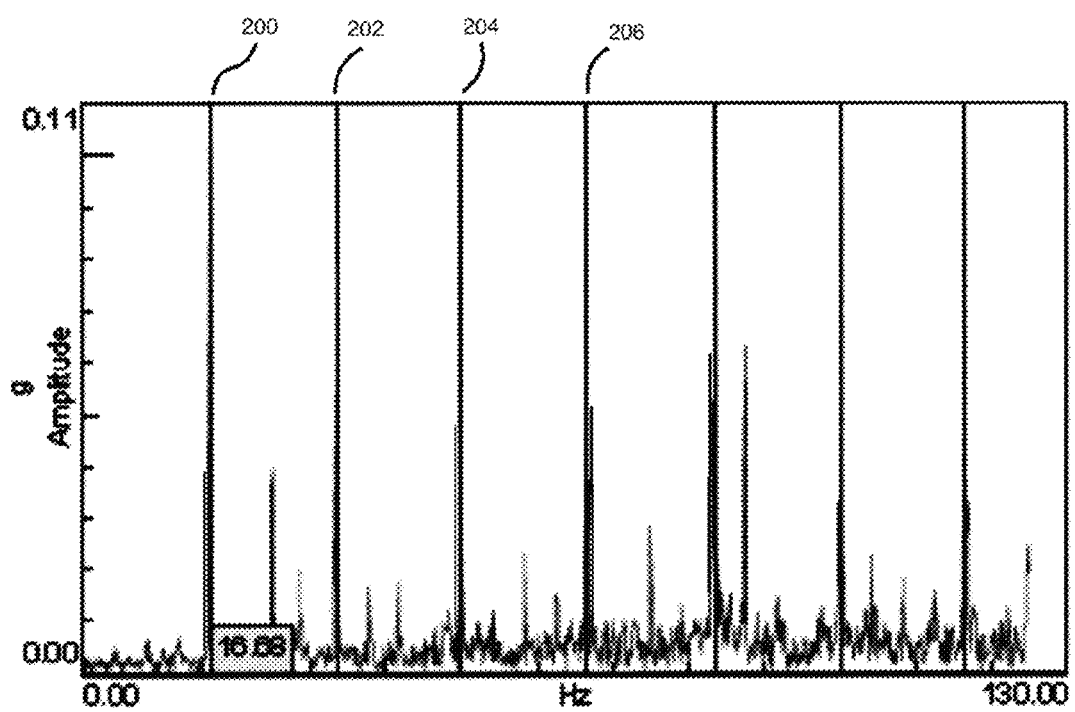

After signals are collected on recorder 136, the recorded signals may be transferred to a CPU for processing and conversion to numeric values indicative of vibrational amplitude of the rotating slinger over the frequency range, and displayed for operator evaluation. As shown in FIGS. 2A and 2B, vibrational amplitude may be plotted over time at a given frequency (FIG. 2A), and vibrational amplitude may be plotted over the frequency range (FIG. 2B). As depicted in FIG. 2B, significant spikes in vibrational amplitude occur at 16.68 Hz, line 200, as well as harmonic frequencies 202, 204 and 206. The graphical representation of vibrational amplitude over the range of frequency in FIG. 2B correspond with the amplitude spike depicted at time 74.08 seconds in FIG. 2A. In FIG. 2A, the RMS value is plotted, as it is a useful measure of amplitude. The RMS value takes into account the time history of the amplitude wave and gives an amplitude value, which is directly related to the energy content, and therefore the destructive abilities of the vibration. In some cases the numerical values, frequency range and time interval may be combined and plotted in a three variable representation to further ease the assessment and identification of harmonics. The vibrational amplitude harmonic spikes may be indicative of a degrading condition of the blending mixer apparatus. In some aspects, the identified harmonics from the numerical values may be used to determine the condition of the rotating slinger, such as erosion of the slinger or impeller due to frictional erosion from sand or other solid particulates. In some other aspects, the identified harmonics may be useful for identifying other conditions which cause the rotating components to be unbalanced, such as loose bolts, bent shafts, damaged gears, drive line issues, impeller damage, worn bearings, and the like.

A database of vibrational amplitude measurements with correlating harmonics may be constructed to provide a baseline of balanced rotating equipment, as well as potential failure harmonic signatures for known unbalanced failure mode. For example, harmonics, or harmonic signatures, may be acquired for known balanced equipment and used as a baseline for analyzing blending mixer performance while in operation, ensuring that new or repaired equipment is properly assembled, or detecting issues during equipment maintenance. In another aspect, vibrational amplitude measurements and correlating harmonics for know failures or near failures may be useful to create harmonic signatures useful for diagnosing potential blending mixer failures for equipment in operation. In some cases, a P-F curve may be created to show that as a failure starts manifesting, the equipment deteriorates to the point at which it can possibly be detected.

Some method embodiments disclosed may be effective in ascertaining the operational efficiency of a blending mixer apparatus. Referring again to FIG. 1, in an operation where sand is mixed with a gel composition to obtain a suitable liquid mixture, the drive shaft 108, slinger 114 and impeller 116 are rotated. Once the slinger 114 and impeller 116 are in motion, a desired charge of solid particulate is dropped into hopper 102, so that the solid particulate flows in a continuous stream through the inlet 106 and drops onto the rotating slinger 114, and propelled outwardly into the casing 104. With the impeller 116 rotating at the same speed as the slinger, the vortex action of the impeller 116 creates a suction force inside the casing, drawing the liquid into the casing through the suction-eye inlet 126. As the liquid is pulled into the casing, the liquid is pressurized by the impeller and interfaces with the solid particulates being flung outwardly from the slinger 114. The effect is a thorough mixing of the solid particulates and liquid composition. Imbalance present in the rotating components can negatively affect the thorough mixing of the solid particulates and liquid, or even the volume ratio thereof. By evaluating the vibrational amplitude over a time interval and frequency range, an operator may ascertain whether the equipment needs repair, or even if the ratio of the solid particulates and liquid need to be adjusted to achieve the suitable mixture.

Figure 3:
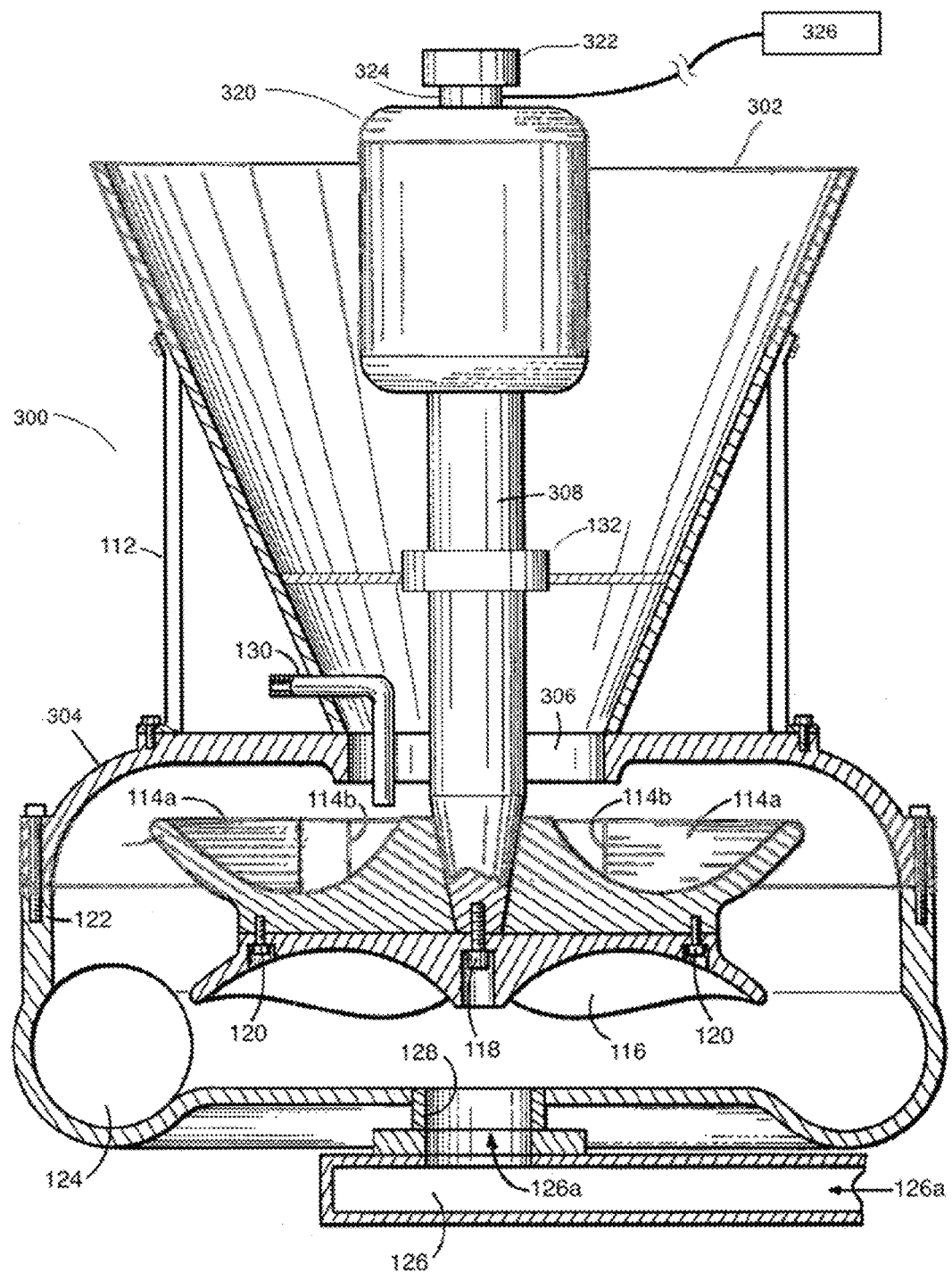
FIG. 3 illustrates general features of an alternate type of blending mixer apparatus useful in some method embodiments of the disclosure, in a cross section view; and, FIG. 4 depicts current draw plotted over a time interval to identify vibrational amplitude and frequency, according to an aspect of the disclosure.

FIG. 3 illustrates general features of an alternate type of blending mixer apparatus useful in some method embodiments of the disclosure. The blending mixer apparatus is generally illustrated by the number 300. The blending mixer may include, although is not limited to, many similar components as the apparatus depicted in FIG. 1, such as hopper 302 mounted on the top side of the blending mixer casing 304 and disposed over opening 306. Rotating drive shaft 308 is positioned inside the hopper 302 and extends through the inlet eye 306 and into the casing 304. Disposed at the bottom of drive shaft 308 are a rotatable slinger member 314 and an impeller member 316. An electric motor 320 for driving the shaft 308 is mounted at the top end of the shaft 308. Electric motor 320 is connected with a variable frequency drive 322 for controlling the electric motor, and a hall effect sensor 324 is disposed between the variable frequency drive 322 and the electric motor 320.

The hall effect sensor 324 is a transducer that varies its output voltage in response to a varying magnetic field generated by variation in current drawn by electric motor 320. Hall effect sensor 324 may be used for sensing such a variation in current in this embodiment, and produces a voltage signal signature over time, which is indicative of the current drawn by the electric motor 320 over time. Repeating spikes of current draw while in operation may be indicative of acceleration of the rotating slinger 314 due to an out of balance condition. The voltage signal signature may be recorded over a time interval on recorder 326 connected with the hall effect sensor 324. After signals are collected on recorder 326, the recorded signals may be transferred to a CPU for processing and conversion to numeric values indicative of a vibrational condition of the rotating slinger over a time interval, and displayed for operator evaluation.

Figure 4:
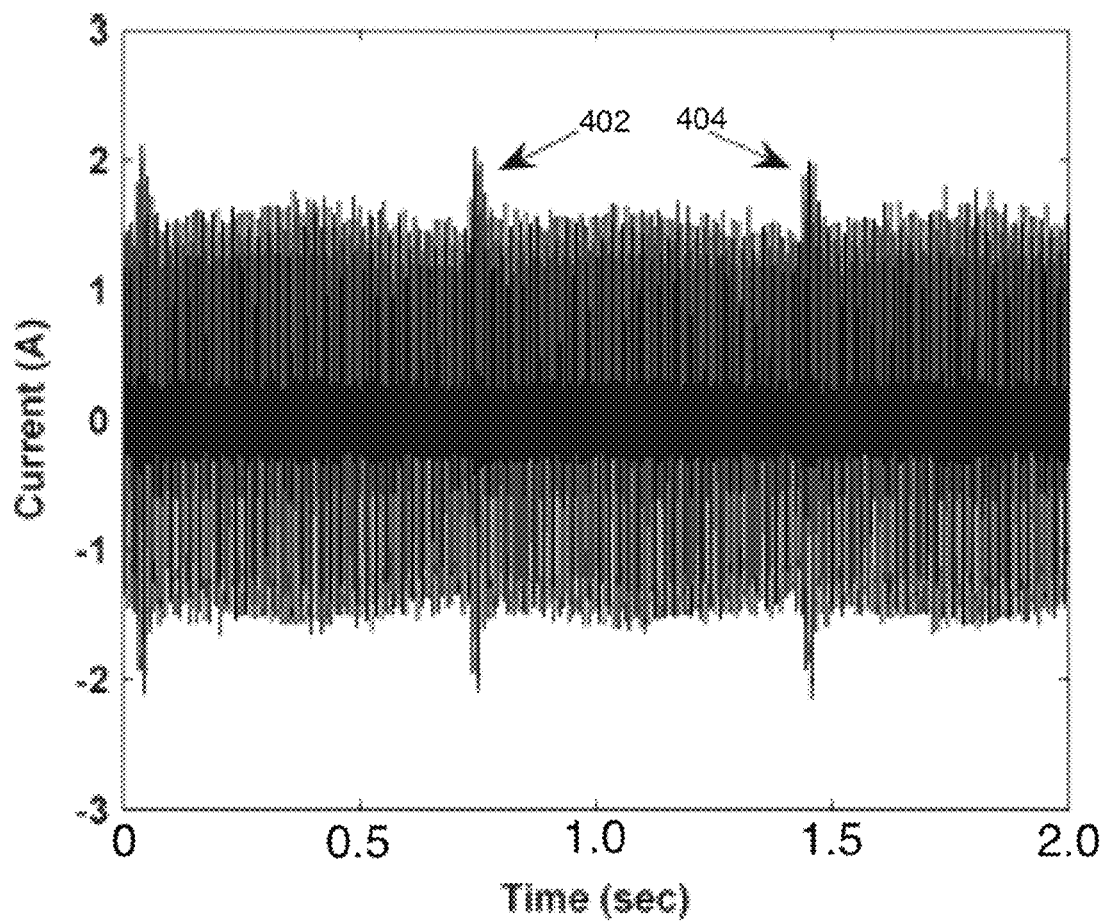

As shown in FIG. 4, current draw measured by hall effect sensor 324 may be plotted over a time interval, and spikes 402 and 404 could correlate to vibrational amplitude and frequency. As shown in FIG. 4, significant spikes in vibrational amplitude occur at about 0.75 seconds and about 1.5 seconds. The repeating pattern of spikes may indicate an out of balance condition of a rotating component in the equipment, such as am eroded rotating slinger, other unbalanced rotating components, loose bolts, bent shafts, drive line issues, impeller damage, worn bearings, and the like.

While embodiments disclosed herein describe blending mixer apparatus and rotating components therein, the disclosure is not only limited to such apparatus, but may also be applied to other rotating equipment such as cement blending equipment, centrifugal pumps, and the like. Embodiments according to the disclosure provide a non-instrusive process to detect unbalanced or otherwise damage conditions which may be measured by devices integrated into the equipment, partially integrated, and in some cases mobile or portable devices for simple attachment and removal after measurements are made. In some aspects, portable components may be hand held equipment.

The foregoing description of the embodiments has been provided for purposes of illustration and description. Example embodiments are provided so that this disclosure will be sufficiently thorough, and will convey the scope to those who are skilled in the art. Numerous specific details are set forth such as examples of specific components, devices, and methods, to provide a thorough understanding of embodiments of the disclosure, but are not intended to be exhaustive or to limit the disclosure. It will be appreciated that it is within the scope of the disclosure that individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Also, in some example embodiments, well-known processes, well-known device structures, and well-known technologies are not described in detail. Further, it will be readily apparent to those of skill in the art that in the design, manufacture, and operation of apparatus to achieve that described in the disclosure, variations in apparatus design, construction, condition, erosion of components, gaps between components may present, for example.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Although a few embodiments of the disclosure have been described in detail above, those of ordinary skill in the art will readily appreciate that many modifications are possible without materially departing from the teachings of this disclosure. Accordingly, such modifications are intended to be included within the scope of this disclosure as defined in the claims.

What is claimed is:

1. A method of analyzing blending mixer performance, the method comprising:
   providing an apparatus for blending solid particles with a liquid composition, the apparatus comprising a rotating slinger, at least one accelerometer adjacent a rotating component for producing a signal that is proportional to an acceleration of the rotating slinger over a frequency range, and a recorder for receiving and storing the signal;

recording the signal over a time interval on the recorder;

converting the recorded signal to numeric values indicative of a vibrational amplitude of the rotating slinger over the frequency range; and, identifying harmonics from the numerical values to determine a condition of the rotating slinger.

2. The method of claim 1 wherein the acceleration correlates with a centrifugal force generated by an imbalance of the rotating slinger.

3. The method of claim 1 further comprising comparing the numeric values with a baseline data set to determine the condition.

4. The method of claim 1 wherein the condition is imbalance.

5. The method of claim 1 further comprising comparing the numeric values with a p-f curve to predict a potential mode of failure.

6. The method of claim 1 wherein the at least one accelerometer is a tri-axial accelerometer.

7. The method of claim 6 wherein the at least one accelerometer further produces a signal that is proportional to an axial acceleration of the rotating slinger over the frequency range.

8. The method of claim 7 further comprising converting the recorded signal to numeric values indicative of an axial vibrational amplitude of the rotating component over the frequency range, and identifying harmonics from the numeric values to determine the condition of the rotating component.

9. A method of predicting mixer failure, the method comprising:

providing a mixing apparatus comprising a rotating component, at least one accelerometer adjacent a rotating component for producing a signal that is proportional to an acceleration of the rotating component over a frequency range, and a recorder for receiving and storing the signal;

recording the signal over a time interval on the recorder;

converting the recorded signal to numeric values indicative of a vibrational amplitude of the rotating component over the frequency range; and, identifying harmonics from the numeric values to determine a condition of the rotating component.

10. The method of claim 9 wherein the rotating component is a rotating slinger and the acceleration correlates with a centrifugal force generated by an imbalance of the rotating slinger.

11. The method of claim 9 further comprising comparing the numeric values with a baseline data set to determine the condition.

12. The method of claim 9 wherein the condition is imbalance.

13. The method of claim 9 further comprising comparing the numeric values with a p-f curve to predict a potential mode of failure.

14. The method of claim 9 wherein the at least one accelerometer is a tri-axial accelerometer.

15. The method of claim 14 wherein the at least one accelerometer further produces a signal that is proportional to an axial acceleration of the rotating component over the frequency range.

16. The method of claim 15 further comprising converting the recorded signal to numeric values indicative of an axial vibrational amplitude of the rotating component over the frequency range, and identifying harmonics from the numeric values to determine a condition of the rotating component.

17. A method of analyzing blending mixer performance, the method comprising:

providing an apparatus for blending solid particles with a liquid composition, the apparatus comprising a rotating slinger, an electric motor for driving the rotating slinger, a variable frequency drive controlling the electric motor, a hall effect sensor disposed between the variable frequency drive and the electric motor, wherein the hall effect sensor produces a signal that is proportional to an acceleration of the rotating slinger;

recording the signal over a time interval on a recorder connected with the hall effect sensor;

converting the recorded signals to numeric values indicative of a vibrational amplitude of the rotating slinger; and, identifying patterns from the numerical values to determine the condition of the rotating slinger.

18. The method of claim 17 wherein the acceleration correlates with a centrifugal force generated by an imbalance of the rotating slinger.

19. The method of claim 17 further comprising comparing the numeric values with a baseline data set to determine the condition.

20. The method of claim 17 wherein the condition is imbalance.

21. The method of claim 17 further comprising comparing the numeric values with a p-f curve to predict a potential mode of failure.

* * * * *